United States Patent [19]

McCarthy

[11] 4,099,525

[45] Jul. 11, 1978

[54] ANIMAL LEG BRACE

[76] Inventor: Robert O. McCarthy, 25 James Ave., Medfield, Mass. 02052

[21] Appl. No.: 775,329

[22] Filed: Mar. 7, 1977

[51] Int. Cl.² .............................................. A61F 5/04
[52] U.S. Cl. ...................................... 128/87 R; 54/82
[58] Field of Search .................. 128/87 R, 88, 89, 83; 54/82, 65

[56] References Cited

U.S. PATENT DOCUMENTS

| 837,719 | 12/1906 | Piccone | 54/82 |
| 1,163,952 | 12/1915 | Richardson | 54/82 |
| 1,256,895 | 2/1918 | Handyside | 54/82 |
| 4,029,090 | 6/1977 | Dawson, Jr. | 128/87 R |

Primary Examiner—John D. Yasko
Attorney, Agent, or Firm—Scott R. Foster

[57] ABSTRACT

An equine animal leg brace comprising a rigid elongated support member, a shoe attached to one end of the support member and adapted to be fixed to a bottom surface of a hoof of an animal, a frame attached to the support member and adapted to be fixed to a leg of the animal by a cast encompassing the leg and the frame, the frame being movably disposed on the support member, and a lock device for fixing the frame in a selected position on the support member.

8 Claims, 2 Drawing Figures

U.S. Patent    July 11, 1978    4,099,525
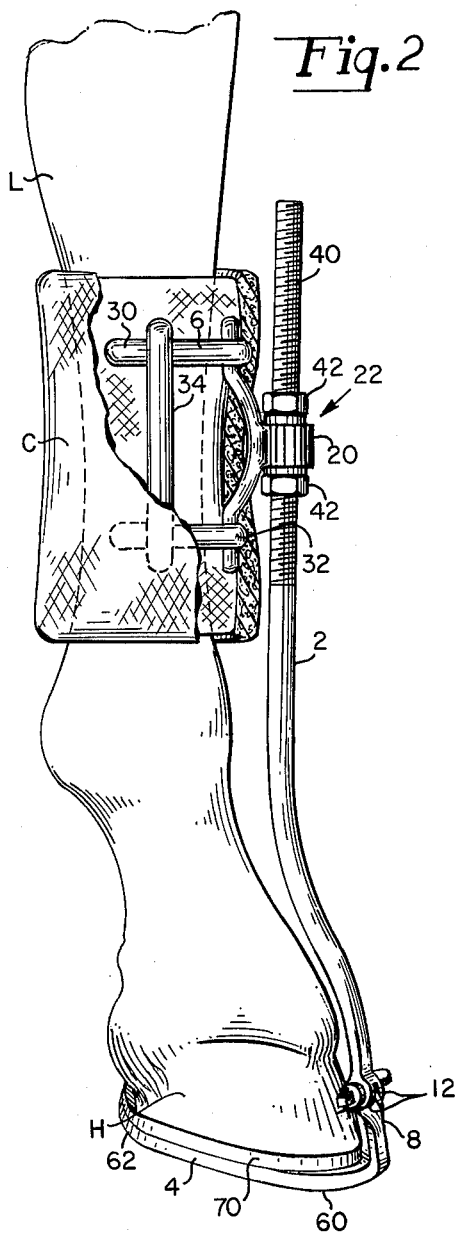
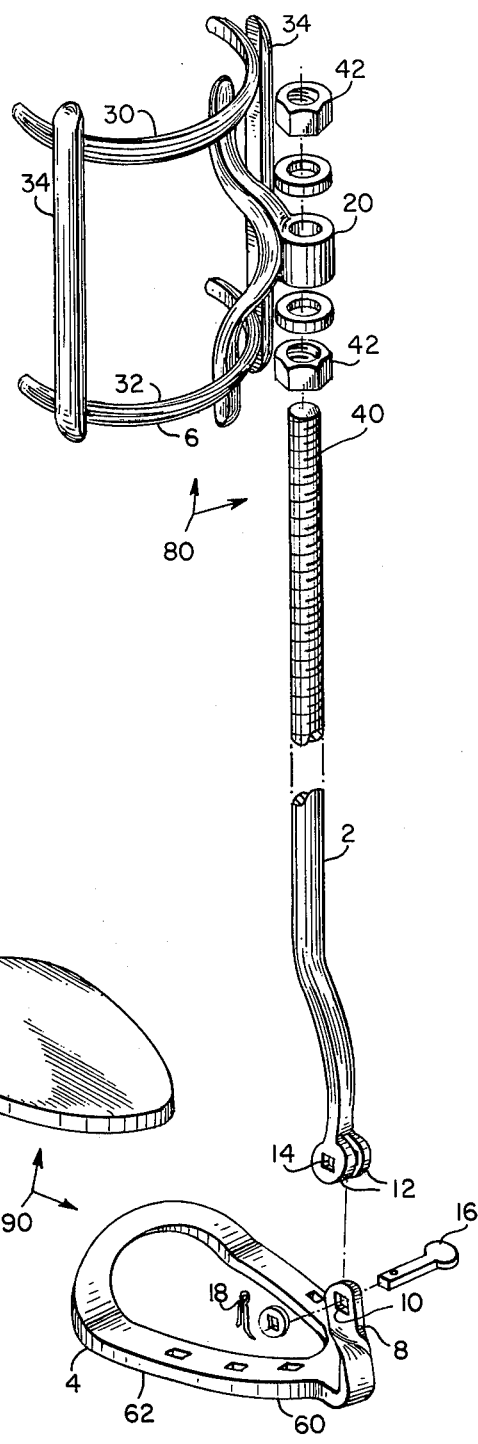

ANIMAL LEG BRACE

BACKGROUND OF THE INVENTION

1. Field of the Invention

This invention relates to braces for veterinary use and is directed more particularly to leg braces for equine animals.

2. Description of the Prior Art

In horses, contraction of flexor tendons, either congenital or acquired, may involve the deep digital flexor tendons and/or superficial digital flexor tendons, both of which are disposed in the back portion of the leg and running generally parallel with the axis of the leg. The degree of contraction is highly variable. Congenital types may result from inherited disorders, mal-position of the fetus in the uterus, or nutritional deficiency in the mare. Acquired contraction may result from an injury that causes decreased use of the limb or from post-fetal nutritional deficiency. If the deep digital flexor tendon is affected, the heel may lift off the ground.

In such instances, the horse will tend to walk upon the toe portion of the hoof concerned, the contracted tendons raising the heel portion of the hoof so that it fails to make contact with the ground. To correct this malady, it is necessary that the affected tendons be stretched or extended over a period of time and strengthened in proper use so that the horse resumes using the entire bottom surface of the hoof.

It has been known to use a rigid U-shaped brace in which the bend of the U is disposed beneath the hoof and the two legs of the U extend upwardly on either side of the horse's leg, the two upper ends of the U-shaped brace being fixed to the horse's leg by a cast encompassing the horse's leg and the two brace ends. Generally, a wire is used to pull the back of the hoof toward the brace, the wire being periodically adjusted to force the back of the hoof downwardly. While some successes have been realized with this device, there are difficulties inherent in its use which the present invention seeks to alleviate. The portion of the brace beneath the hoof presents the horse with an unusual elevation which the horse may attempt to adjust to by compensation in a manner causing other injury or strain. Secondly, affixing and adjusting the wire to the hoof and the brace is an inexact manual operation, done mostly by guess as to degree. And thirdly, the two upstanding legs of the U-shaped brace provide insufficient support for a well mounted cast.

SUMMARY OF THE INVENTION

It is an object of the invention to provide a leg brace for correcting contracted tendons in equine animals.

A further object of the invention is to provide such a brace allowing a normal disposition of the affected hoof relative to the ground, i.e., a brace not incurring unnatural elevation of the hoof.

A still further object of the invention is to provide such a brace in which there is provided ample foundation for application of a cast thereto.

Another object of the invention is to provide such a device having facility for uniform periodic adjustments so as to permit uniform extension of tendons over a period of time.

Another object of the invention is to provide such a device in which there is a degree of universality, to facilitate preparation thereof well in advance of application.

Still another object of the invention is to provide such a device as can be applied, in part, in a manner to which most horses are familiar and which therefor would not be unduly distressing to them.

With the above and other objects in view, as will hereinafter appear, a feature of the present invention is the provision of an equine animal leg brace comprising a rigid elongated support member, a shoe attached to one end of the support member and adapted to be fixed to a bottom surface of a hoof of an animal, a frame attached to the support member and adapted to be fixed to a leg of the animal by a cast encompssing the leg and the frame, the frame being movably disposed on the support member, and lock means for fixing the frame in a selected position on the support member.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention from which its novel features and advantages will be apparent.

FIG. 1 is a perspective exploded view of one form of leg brace illustrative of an embodiment of the invention; and FIG. 2 is an elevational view of the device of FIG. 1, shown in place on a leg of an animal.

DESCRIPTION OF THE PREFERRED EMBODIMENT

Referring to the drawings, it will be seen that the invention comprises a rigid elongated support member 2, which may be of metal, such as steel. Attached to a first or lower end of the support member 2 is a shoe 4 adapted to be fixed to the bottom of a hoof H. A rigid cast frame 6 is attached to the support member 2 and is adapted to be fixed to the leg L of an animal by way of a plaster cast C encompassing the leg L and the frame 6.

The shoe 4 may be an ordinary or modified horseshoe, many varieties of which are well known in the art, but including a forwardly and upwardly projecting flange 8 having therein a substantially square-shaped aperture 10. The first end of the support member 2 is provided with a bifurcated extension 12, having therein substantially square-shaped apertures 14. To connect the shoe 4 to the support member 2, the apertures 10, 14 are aligned, the flange 8 being inserted between the bifurcations of the extension 12. A loose-fitting, substantially square-shaped pin 16 is inserted in the apertures 10, 14 and a cotter-pin 18 inserted in the pin 16 to secure the pin 16 in place.

The cast frame 6 is movably secured on the support member 2 by a lug 20 extending from the frame 6 and having a hole therein which receives the support member 2. Lock means 22 are provided for fixing the frame 6 on the member 2, to selectively position the frame 6 on the member 2.

The cast frame 6 comprises an upper curved rigid member 30 and a lower curved rigid member 32 interconnected by a plurality of straight rigid members 34. The members 30, 32, and 34 may be metal, such as steel.

A portion 40 of the support member 2 is threaded, the hole of the lug 20 being of such diameter as to be slidably movable thereover. The locking means 22 comprises internally threaded nuts 42 on either side of the lug 20. Threaded movement of the nuts 42 determine the position of the lug 20 on the member 2 and thereby the position of the frame 6 on the member 2.

The shoe 4 may be provided with a toe portion 60 of greater thickness than that of the heel portions 62, to encourage further stretching of the affected tendons. A plate 70 may be used between the shoe 4 and the hoof to protect the sole of the hoof and insure against bruises and the like while the animal is becoming accustomed to use of the whole bottom of the hoof. The plate may be of an elastomeric material.

In operation, a farrier preparing in advance for application of such a brace might have in stock a support member and frame assembly 80 comprising the support member 2 and frame 6, as described above. He might have in stock shoe assemblies 90 comprising a shoe 4, with lug 8, and if desired a plate 70, all as described above.

In application to an animal, the shoe 4 and plate 70 are shaped and applied as would be an ordinary shoe and pad. In most instances, the animal is used to shoeing and is not unduly alarmed by this procedure. A cast C is then applied to the leg L, the cast including the rigid frame 6. The cast is normally applied below the knee and above the ankle so as to leave free the joints of the animal whereby again, not to unduly confine and alarm the animal. The support member is then shaped, if necessary, to accommodate the leg, as by increasing or decreasing a bend in the support and is then slid upwardly through the hole in the lug 20, the support having the lower nut 42 thereon. The upper nut 42 is then loosely threaded onto the upper end of the support member 2. The bifurcated extension 12 at the lower end of the support member 2 is then connected to the shoe 4 by way of the pin 16, as described above. The nuts 42 are then threaded downwardly, thereby causing the support member 2 to be drawn upwardly. Upward movement of the support member 2 causes upward movement of the toe portion 60 of the shoe 4, and thereby toe portion of the hoof H of the animal, and consequent downward movement of the heel portions 62 of the shoe 4 and thereby of the heel portion of the hoof, stretching the aforesaid tendons in the back of the animal's leg.

At the first application, the support member 2 exerts a very slight pulling force on the top of the hoof. Each day, however, the nuts 42 may be turned a selected distance, as for example, one turn per day, to gradually raise the toe and lower the heel of the hoof, to extend the tendons. If at any time the animal becomes distressed by the tension on the hoof, a quick removal of the cotter-pin 18 and pin 16 releases the shoe 4 from the support member 2.

The above-mentioned square apertures 10, 14 and loose-fitting square-shaped pin 16 permit some pivotal movement but limit the degree of pivotal movement about the pin 16, thereby limiting the tendon extension at any one time to a minimal increment, an excessive extension at any one time being deleterious to the correction process and possibly resulting in pulled, or "bowed" tendons which in turn would render the animal lame.

In practice, it has been found preferable to leave the device on the animal for about twelve hours and to remove the device for about twelve hours per day, although a program for a particular animal would vary in accordance with the physical characteristics and attitude of the animal, as well as the judgment of the attending veterinarian and/or farrier, etc.

If desired, a boot (not shown) may be placed over the affected hoof, shoe, and lower parts of the support member to protect the entire hoof and assembly from damage.

While reference has been made to equine animals and more specifically horses, it will be apparent that the present invention might be used on virtually any hooved animal having similar characteristics, as for example, cattle, deer, buffalo, and the like.

It is to be understood that the present invention is by no means limited to the particular construction herein disclosed and/or shown in the drawings, but also comprises any modifications or equivalents within the scope of the disclosure.

Having thus described my invention what I claim as new and desire to secure by Letters Patent of the United States is:

1. An equine animal leg brace comprising a rigid elongated support member, a shoe attached to a first end of said member and adapted to be fixed to a bottom surface of a hoof of an animal, a rigid cast frame attached to said member and adapted to be fixed to a leg of said animal by a cast encompassing said leg and said frame, said cast frame being movably disposed on said support member, and lock means for fixing said cast frame on said support member, whereby to facilitate selective positioning of said cast frame on said support member.

2. The invention according to claim 1 in which said shoe is attached to said first end of said support member by means permitting limited pivotal movement of said shoe relative to said support member.

3. The invention according to claim 1 in which said cast frame comprises an upper curved rigid member, a lower curved rigid member, a plurality of rigid members interconnecting said first and second curved members, and a support mounting means extending from said cast frame and slidably disposed upon said support member.

4. The invention according to claim 3 in which a portion of said support member is threaded and said support mounting means is slidable thereover, and said lock means comprises internally threaded members threadedly movable on said threaded portion of said support member to lock said support mounting means in a selected position on said support member.

5. The invention according to claim 2 in which said shoe is provided with a first flange having a first substantially square aperture therein, said first end of said support member is provided with second flange means having a second substantially square aperture therein, said first and second apertures being in substantial alignment, and substantially square pin means extending through said first and second apertures and being of a width less than the width of said apertures.

6. The invention according to claim 5 in which said shoe is of a thickness at the toe portion thereof exceeding the thickness at the heel portions thereof.

7. The invention according to claim 6 including a plate member disposed on upper surfaces of said shoe and adapted to be disposed adjacent said hoof.

8. The invention according to claim 5 in which said second flange means comprises a bifurcation defining two flanges, each of said flanges having a substantially square aperture therein, each of said second flange means apertures being in substantial alignment with said first aperture.

* * * * *